United States Patent
Gale et al.

(10) Patent No.: US 8,894,900 B2
(45) Date of Patent: Nov. 25, 2014

(54) STENT WITH FLEXIBLE SECTIONS IN HIGH STRAIN REGIONS

(75) Inventors: David C. Gale, San Jose, CA (US);
Klaus Kleine, Los Gatos, CA (US);
Anthony J. Abbate, Santa Clara, CA (US); Svava Maria Atladottir, Burlingame, CA (US); Stephen Pacetti, San Jose, CA (US)

(73) Assignee: Advanced Cardiovascular Systems Inc., Santa Clara, CA (US)

( * ) Notice: Subject to any disclaimer, the term of this patent is extended or adjusted under 35 U.S.C. 154(b) by 770 days.

(21) Appl. No.: 12/247,164

(22) Filed: Oct. 7, 2008

(65) Prior Publication Data
US 2009/0036972 A1  Feb. 5, 2009

Related U.S. Application Data

(62) Division of application No. 11/141,834, filed on May 31, 2005, now abandoned.

(51) Int. Cl.
*B29C 70/74* (2006.01)

(52) U.S. Cl.
USPC .......................................... 264/154; 264/267

(58) Field of Classification Search
None
See application file for complete search history.

(56) References Cited

U.S. PATENT DOCUMENTS

| | | | | |
|---|---|---|---|---|
| 5,922,020 | A * | 7/1999 | Klein et al. | 623/1.15 |
| 6,293,967 | B1 * | 9/2001 | Shanley | 623/1.15 |
| 6,562,065 | B1 * | 5/2003 | Shanley | 623/1.15 |
| 6,663,664 | B1 * | 12/2003 | Pacetti | 623/1.2 |
| 6,758,859 | B1 | 7/2004 | Dang et al. | |
| 2003/0009214 | A1 | 1/2003 | Shanley | |
| 2003/0181972 | A1 | 9/2003 | Jansen et al. | |
| 2004/0088041 | A1 * | 5/2004 | Stanford | 623/1.15 |
| 2004/0098117 | A1 | 5/2004 | Hossainy et al. | |
| 2005/0273157 | A1 | 12/2005 | Pinchasik | |
| 2006/0025852 | A1 | 2/2006 | Amstrong et al. | |
| 2006/0271161 | A1 | 11/2006 | Meyer et al. | |

FOREIGN PATENT DOCUMENTS

WO  WO 03/047463  6/2003

\* cited by examiner

*Primary Examiner* — Edmund H. Lee
(74) *Attorney, Agent, or Firm* — Squire Patton Boggs (US) LLP (57) ABSTRACT

A stent for treating a bodily lumen with a flexible section in a high strain region is disclosed. A flexible section may be selectively positioned to reduce an amount of strain in the high strain region when subjected to the applied stress during use to inhibit or prevent fracturing in the high strain region.

7 Claims, 3 Drawing Sheets

STENT WITH FLEXIBLE SECTIONS IN HIGH STRAIN REGIONS

This application is a divisional application of U.S. application Ser. No. 11/141,834, filed May 31, 2005 now abandoned, which is incorporated herein by reference in its entirety.

BACKGROUND OF THE INVENTION

1. Field of the Invention

This invention relates to implantable medical devices, such as stents. In particular the invention relates to stents having structural elements with flexible or deformable sections that increase the crack resistance of the stent during use.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may be also be described as, hoop or circumferential strength and rigidity.

Additionally, the stent should also be longitudinally flexible to allow it to be maneuvered through a tortuous vascular path and to enable it to conform to a deployment site that may not be linear or may be subject to flexure. The material from which the stent is constructed must allow the stent to undergo expansion. Once expanded, the stent must maintain its size and shape throughout its service life despite the various forces that may come to bear on it, including the cyclic loading induced by the beating heart. Finally, the stent must be biocompatible so as not to trigger any adverse vascular responses.

The structure of a stent is typically composed of scaffolding that includes a pattern or network of interconnecting structural elements or struts. The scaffolding can be formed from wires, tubes, or sheets of material rolled into a cylindrical shape. The scaffolding is designed so that the stent can be radially contracted (to allowed crimping) and radially expanded (to allow deployment). A conventional stent is allowed to expand and contract through movement of individual structural elements of a pattern with respect to each other. Such movement typically results in substantial deformation of localized portions of the stent's structure.

Stents have been made of many materials such as metals and polymers, including biodegradable polymeric materials. An advantage of stents fabricated from polymers is that they can be designed to have greater flexibility than metal stents. However, a potential problem with polymeric stents is that their struts may be susceptible to cracking during crimping and expansion especially for brittle polymers. The localized portions of the stent pattern subjected to substantial deformation tend to be the most vulnerable to failure.

Therefore, it would be desirable reduce or eliminate the susceptibility of cracking in a polymeric stent, particularly in localized regions of high deformation. It is also desirable to maintain or increase their flexibility while improving crack resistance.

SUMMARY OF THE INVENTION

The present invention is directed to embodiments of a stent having structural elements that may include a flexible or deformable section embedded within a high strain region of a structural element. The flexible section may extend through the high strain region from an abluminal surface of the high strain region to a luminal surface of the high strain region. The flexible section may have a greater flexibility than a majority of the structural element outside of the flexible section. The high strain region may have a higher strain as compared to other regions of the structural element when the stent is subjected to an applied stress during use. The section may be selectively positioned to increase resistance to strain in the high strain region to inhibit or prevent fracturing in the high strain region when subjected to the applied stress during use.

A further aspect of the invention is directed to embodiments of a method of forming a stent. The method may include forming a cavity within a high strain region of a structural element. The cavity may extend through the high strain region from an abluminal surface of the high strain region to a luminal surface of the high strain region. The high strain region may include a higher strain as compared to other regions of the structural element when the stent is subjected to an applied stress during use. The method may further include forming a flexible section within all or substantially all of the cavity. The flexible section may have a greater flexibility than a majority of the structural element outside of the flexible section. The section may be selectively positioned to reduce an amount of strain in the high strain region to inhibit or prevent fracturing in the high strain region when subjected to the applied stress during use.

DETAILED DESCRIPTION OF THE INVENTION

For the purposes of the present invention, the following terms and definitions apply:

The "glass transition temperature," $T_g$, is the temperature at which the amorphous domains of a polymer change from a brittle vitreous state to a solid deformable or ductile state at atmospheric pressure. In other words, the $T_g$ corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. $T_g$ of a given polymer can be dependent on the heating rate and can be influenced by the thermal history of the polymer. Furthermore, the chemical structure of the polymer heavily influences the glass transition by affecting mobility.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

Furthermore, a property of a material that quantifies a degree of strain with applied stress is the modulus. "Modulus" may be defined as the ratio of a component of stress or force per unit area applied to a material divided by the strain along an axis of applied force that results from the applied force. For example, a material has both a tensile and a compressive modulus. A material with a relatively high modulus tends to be stiff or rigid. Conversely, a material with a relatively low modulus tends to be flexible. The modulus of a material depends on the molecular composition and structure, temperature of the material, and the strain rate or rate of deformation. For example, below its $T_g$, a polymer tends to be brittle with a high modulus. As the temperature of a polymer is increased from below to above its $T_g$, its modulus decreases.

The "ultimate strength" or "strength" of a material refers to the maximum stress that a material will withstand prior to fracture. A material may have both a tensile and a compressive strength. The ultimate strength may be calculated from the maximum load applied during a test divided by the original cross-sectional area.

The term "elastic deformation" refers to deformation of an object in which the applied stress is small enough so that the object moves towards its original dimensions or essentially its original dimensions once the stress is released. However, an elastically deformed polymer material may be prevented from returning to an undeformed state if the material is below the $T_g$ of the polymer. Below $T_g$, energy barriers may inhibit or prevent molecular movement that allows deformation or bulk relaxation.

"Elastic limit" refers to the maximum stress that a material will withstand without permanent deformation. The "yield point" is the stress at the elastic limit and the "ultimate strain" is the strain at the elastic limit. The term "plastic deformation" refers to permanent deformation that occurs in a material under stress after elastic limits have been exceeded.

"Neutral axis" refers to a line or plane in a structural member subjected to a stress at which the strain is zero. For example, a beam in flexure due to stress (e.g., at a top face) has tension on one side (e.g., the bottom face) and compression on the other (e.g., the top face). The neutral axis lies between the two sides at a location or locations of zero strain. The neutral axis may correspond to a surface. For a linear, symmetric, homogeneous beam, the neutral axis is at the geometric centroid (center of mass) of the beam. However, the neutral axis for a curved beam does not coincide with the centroidal axis.

The strain increases in either direction away from the neutral axis. The length and strain of material elements parallel to the centroidal axis depend on both the distance of a material element from that axis and the radius of curvature of the curved beam.

In general, polymers can be biostable, bioabsorbable, biodegradable, or bioerodable. Biostable refers to polymers that are not biodegradable. The terms biodegradable, bioabsorbable, and bioerodable, as well as degraded, eroded, and absorbed, are used interchangeably and refer to polymers that are capable of being completely eroded or absorbed when exposed to bodily fluids such as blood and can be gradually resorbed, absorbed and/or eliminated by the body.

A stent made from a biodegradable polymer is intended to remain in the body for a duration of time until its intended function of, for example, maintaining vascular patency and/or drug delivery is accomplished. After the process of degradation, erosion, absorption, and/or resorption has been completed, no portion of the biodegradable stent, or a biodegradable portion of the stent will remain. In some embodiments, very negligible traces or residue may be left behind. The duration is typically in the range of six to eighteen months.

In addition, a medicated stent may be fabricated by coating the surface of a stent with a polymeric carrier. The coating may include a bioactive agent. A "bioactive agent" is a moiety that is mixed, blended, bonded or linked to a polymer coating, or to a polymer from which a stent is made, and provides a therapeutic effect, a prophylactic effect, both a therapeutic and a prophylactic effect, or other biologically active effect upon release from the stent.

Representative examples of polymers that may be used to fabricate embodiments of implantable medical devices disclosed herein include, but are not limited to, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating embodiments of implantable medical devices disclosed herein include ethylene vinyl alcohol copolymer (commonly known by the generic name EVOH or by the trade name EVAL), poly(butyl methacrylate), poly(vinylidene fluoride-co-hexafluoropropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, poly(vinyl acetate), styrene-isobutylene-styrene triblock copolymers, and polyethylene glycol.

The term "implantable medical device" is intended to include, but is not limited to, balloon-expandable stents, self-expandable stents, stent-grafts, and vascular grafts. In general, implantable medical devices, such as stents, can have virtually any structural pattern that is compatible with a bodily lumen in which it is implanted. Typically, a stent is composed of a pattern or network of circumferential and longitudinally extending interconnecting structural elements or struts. In general, the struts are arranged in patterns, which are designed to contact the lumen walls of a vessel and to maintain vascular patency. A myriad of strut patterns are known in the art for achieving particular design goals. A few of the more important design characteristics of stents are radial or hoop strength, expansion ratio or coverage area, and longitudinal flexibility.

Polymer tubes used for fabricating stents may be formed by various methods. These include, but are not limited to extrusion or injection molding. Conventionally extruded tubes tend to possess no or substantially no radial orientation or, equivalently, polymer chain alignment in the circumferential direction.

A tube used for fabricating a stent may be cylindrical or substantially cylindrical in shape. In some embodiments, the diameter of the polymer tube prior to fabrication of an implantable medical device may be between about 0.2 mm and about 10 mm, or more narrowly, between about 1 mm and about 3 mm.

In general, the scaffolding of conventional stents is designed so that the stent can be radially compressed (to allowed crimping) and radially expanded (to allow deployment). A conventional stent expands and contracts through movement of individual structural elements of a pattern with respect to each other.

Medical devices are typically subjected to stress during use, both before and during treatment. "Use" includes manufacturing, assembling (e.g., crimping a stent on a balloon), delivery of a stent through a bodily lumen to a treatment site, and deployment of a stent at a treatment site. The scaffolding or substrate experiences stress that results in deformation or strain in the scaffolding. For example, during deployment, the scaffolding of a stent can be exposed to stress caused by the radial expansion of the stent body. In addition, the scaffolding may be exposed to stress when it is mounted on a catheter from crimping or compression of the stent. During delivery, a stent can be exposed to stress from the flexure of the stent body as it passes through tortuous pathways of a vessel. In addition, after deployment a stent is exposed to stress arising from changes in shape of a vessel induced by the beating of the heart.

These stresses can cause the scaffolding to crack or fracture. Failure of the mechanical integrity of the stent while the stent is localized in a patient can lead to serious risks for a patient. For example, there is a risk of embolization caused by a piece of the polymeric scaffolding breaking off from the stent.

As indicated above, selected regions of a stent may be subjected to relatively high stress and strain when the device is under an applied stress during use. Thus, such regions may have different mechanical requirements than regions that experience relatively low stress and strain.

Generally, the stress and the strain in a stent are not uniformly distributed throughout its structure. Some regions may experience no or substantially no stress and strain, while other portions may experience relatively high stress and strain. As indicated above, certain localized portions of the stent's structure undergo substantial deformation. It is these regions that are the most susceptible to fracture and cracking. The susceptibility to cracking may be reduced by making such regions more resistant to strain.

Unfortunately, many polymers used for stent scaffoldings, are relatively brittle or inelastic at biological conditions. This is particularly true for polymers with a $T_g$ above a body temperature. In this case, the polymer in the stent never reaches its $T_g$, and therefore, the polymer remains relatively inelastic while in the body. Polymers, in general, and many polymers used in scaffoldings for devices tend to have a relatively high degree of inelasticity, and, hence have relatively low strength compared to a metal. Polymers can have an ultimate strain as low as 5% of plastic strain. In general, the ultimate strain for a polymer is highly dependent on material properties including percent crystallinity, orientation of polymer chains, and molecular weight. Therefore, polymer-based scaffoldings are highly susceptible to fracture at regions of a medical device subjected to relatively high stress and strain.

However, it is desirable for certain regions of a device to be relatively stiff or inelastic (high modulus) and strong. Such regions may experience relatively low stress and strain during use, but act as support members that resist radial compressive forces imposed on a deployed stent. Additionally, as discussed above, longitudinal flexibility in a stent facilitates delivery of the stent to a treatment location. Therefore, it is desirable to have a stent that is resistant to cracking in localized regions of high deformation, sufficiently rigid to maintain the structural integrity of the sent, and longitudinally flexible during delivery.

Figure 1A:
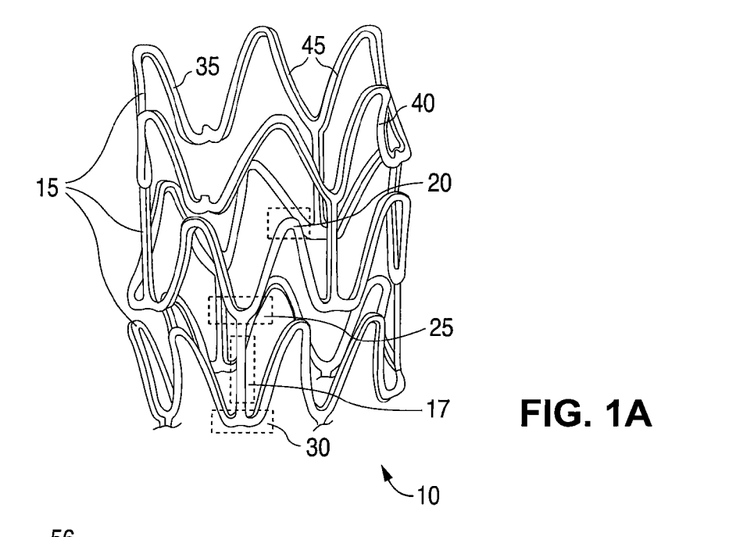
FIG. 1A depicts a stent.

FIG. 1A illustrates a three-dimensional view of a conventional stent 10 with a typical stent pattern. The stent may have a pattern that includes a number of interconnecting elements or struts 15. Variations of the structure of such patterns are virtually unlimited. As shown in FIG. 1A, the geometry or shape of stents vary throughout their structure. A pattern may include portions of struts that are straight or relatively straight, an example being a section 17. In addition, patterns may include struts that include curved or bent portions as in a section 20. Patterns may also include intersections of struts with curved or bent portions as in sections 25 and 30. As shown in FIG. 1A, struts 15 of stent 10 include luminal faces 35, abluminal faces 40, and side-wall faces 45.

Figure 1B:
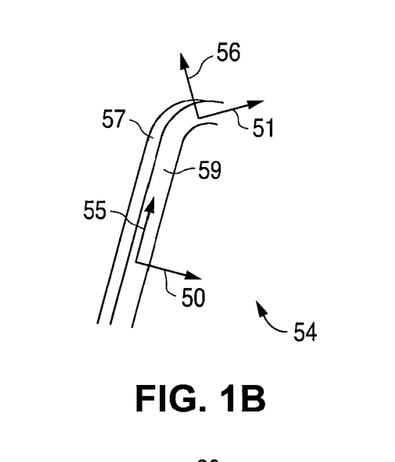
FIG. 1B depicts a three-dimensional view of a portion of a stent.

FIG. 1B depicts a portion 54 of a strut depicting a latitudinal axis 50 and a longitudinal axis 55 along a straight section of portion 54. Portion 54 has an abluminal or luminal face 59 and a sidewall face 57. A longitudinal axis 51 on a curved section of a strut may be defined as a tangent to a curvature at a location on the curved section. A corresponding latitudinal axis 56 is perpendicular to longitudinal axis 51. In other embodiments, a latitudinal cross-section may include any number of faces or be a curved surface.

In some embodiments, a pattern of a stent such as that pictured in FIG. 1A, may be formed from a tube by laser cutting the pattern of struts in the tube. The stent may also be formed by laser cutting a polymeric sheet, rolling the pattern into the shape of the cylindrical stent, and providing a longitudinal weld to form the stent. Other methods of forming stents are well known and include chemically etching a polymeric sheet and rolling and then welding it to form the stent. The stent may be formed by injection molding of a thermoplastic or reaction injection molding of a thermoset polymeric material.

As indicated above, crimping and expansion of a stent with a typical pattern, such as in FIG. 1A, result in localized regions of the pattern having high deformation or strain that are susceptible to failure. The stent pattern depicted in FIG. 1A may be used to illustrate such localized regions. Some portions of a stent pattern may have no or relatively no strain, while others may have relatively high strain. Straight or substantially straight sections of struts such as section 17 of stent 10 in FIG. 1A experience no or relatively no strain. These sections, however, do act as support members that maintain the structural integrity of the stent. On the other hand, sections 20, 25, and 30 may experience relatively high strain when the stent is expanded or crimped.

Figure 2A:
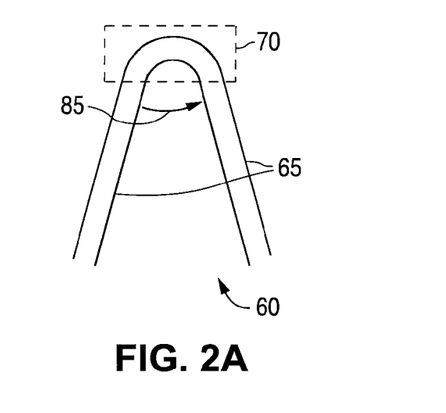
FIG. 2A depicts a side view of a portion of a stent.
Figure 2B:
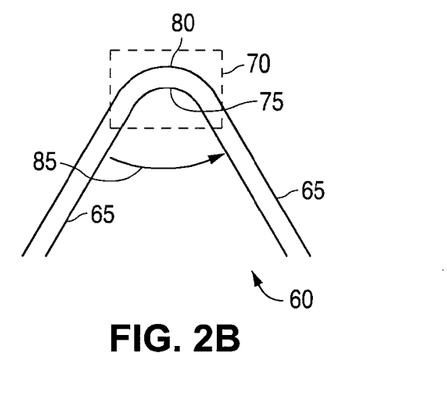
FIG. 2B depicts a side view of an expanded portion of a stent.
Figure 2C:
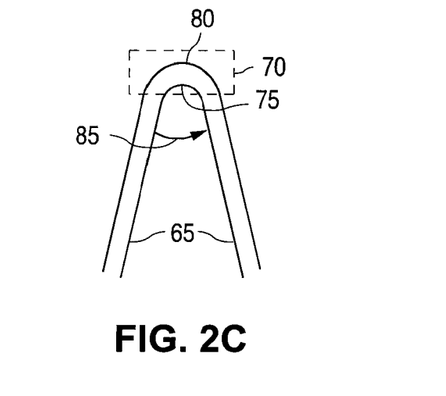
FIG. 2C depicts a side view of a compressed portion of a stent.

For example, FIGS. 2A-C depict partial planar side views of luminal or abluminal surfaces of a portion 60 from a stent in a relaxed state (neither expanded or compressed) that includes straight sections 65 and a curved section 70 with an angle 85. When a stent undergoes radial expansion, portions of struts bend resulting in an increase of angle 85 between straight sections 65, as shown in FIG. 2B.

A bending plane of portion 60 corresponds to the plane through which sections 65 sweep through as they bend. For example, the bending plane may correspond to the plane of the sheet of paper. Thus, the abluminal and luminal surfaces may be substantially parallel to the bending plane of the bending portions of structural elements such as portion 60.

FIGS. 2B-C depict portion 60 in a plane of bending. Radial expansion of a stent causes substantially no strain in straight sections 65. However, the bending of section 60 causes relatively high stress and strain in curved section 70. As illustrated in FIG. 2B, when a stent is expanded a concave portion 75 of curved section 70 experiences relatively high tensile stress and strain and a convex portion 80 of curved section 70 experiences relatively high compressive stress and strain. As shown in FIG. 2C, when a stent is crimped, angle 85 decreases and concave portion 75 experiences relatively high compressive strain and convex portion 80 experiences relatively high tensile strain.

Figure 3:
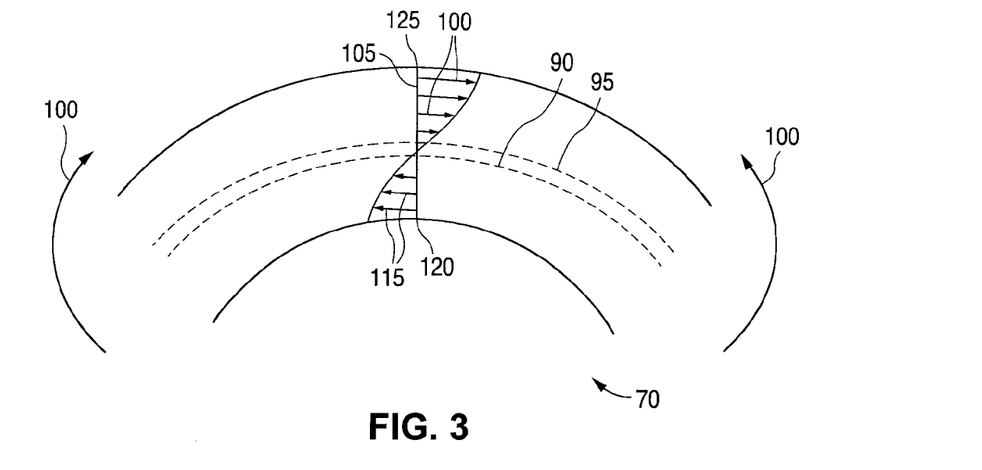
FIG. 3 depicts an expanded view of curved portion of a stent.

FIG. 3 depicts an expanded view of curved section 70 with a neutral axis 90 indicated. As indicated above, the strain along the neutral axis is zero. For a strut that is symmetric along its longitudinal and latitudinal axis, the neutral axis may be a surface perpendicular to a plane of bending (i.e., perpendicular to the plane of the sheet of paper). Additionally, as in a curved beam, a centroidal axis 95 of a curved section of a strut, such as section 70, does not coincide with the neutral axis. Therefore, in a small, narrow region of curved section 70 along neutral axis 90, there is zero or relatively low strain.

Furthermore, the strain in a structural element or beam increases with distance from the neutral axis. Therefore, the strain in section 70 depends on distance from the neutral axis 90 and the change in curvature from an equilibrium or unstressed curvature of section 70. For instance, a bending moment 100 that tends to straighten section 70, as in FIG. 2B, results in strain above and below the neutral axis. The magnitude of the strain as a function of the distance from the neutral axis at a plane 105 is illustrated by arrows 110 and 115. Above neutral axis 90, the strut is in compression with a compressive strain that increases with distance from neutral axis 90, as shown by arrows 110. Below neutral axis 90 the strut is in tension with a tensile strain that increases with distance from neutral axis 90, as shown by arrows 115. Similarly, a bending moment that tends to increase the bend in section 70, as in FIG. 2C, will result in tension above the neutral axis and compression below the neutral axis.

In general, the greater the change in curvature of a curved portion of a strut due to an applied stress, the larger the magnitude of the strain at a given distance away from the neutral axis (See arrows 120 and 125 in FIG. 3). The maximum tensile and compressive strain occur the edges of a structural element. In FIG. 3, the maximum tensile and compressive strain along plane 105 is at 120 and 125, respectively.

Furthermore, the magnitude of the strain in a bending element or beam varies along the longitudinal axis of the element. The maximum strain tends to occur at a center of symmetry of the bending element. The strain tends to decrease along the longitudinal axis with distance going away from the center of symmetry of the bend. For example, if plane 105 is a center of symmetry of bending, the strain decreases with distance away from plane 105 along a longitudinal axis of section 70 at a fixed distance from neutral axis 90.

Figure 4:
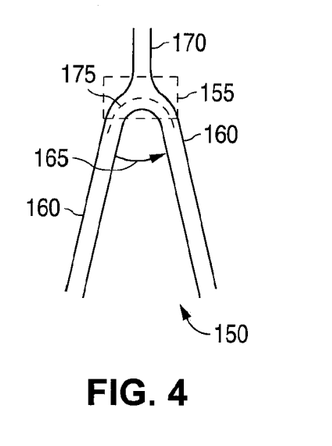
FIG. 4 depicts a side view of a portion of a stent.

FIG. 4 depicts a partial planar side view of a portion 150 from a stent in an unstressed state that includes curved section 155, straight sections 160 at an angle 165, and straight section 170. Radial expansion of the stent increases angle 165 and crimping decreases angle 165. The stress and strain in straight sections 160 and 170 is relatively small. When a stent is expanded, section 155 has relatively high tensile stress and strain above a neutral axis 175 and relatively high compressive stress and strain below neutral axis 175. Alternatively, when a stent is expanded, section 155 has relatively high tensile stress and strain below neutral axis 175 and relatively high compressive stress and strain above neutral axis 175.

Figure 5:
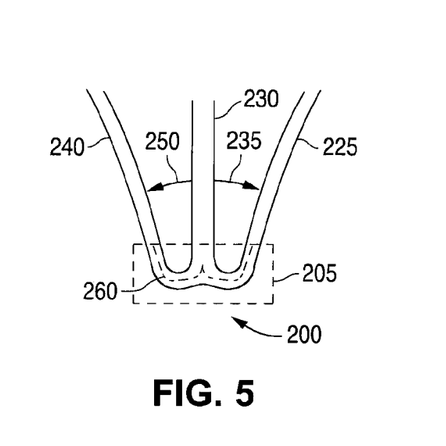
FIG. 5 depicts a side view of a portion of a stent.

FIG. 5 depicts a partial planar side view of a portion 200 from a stent in an unstressed state that includes a curved section 205, straight sections 225, 230, and 240. Straight sections 225 and 230 are at an angle 235 and straight sections 230 and 240 are at an angle 250. Radial expansion of the stent increases angles 235 and 250 and crimping decreases angles 235 and 250. The stress and strain in straight sections 225, 230, and 240 is relatively small. When a stent is expanded, section 205 has relatively high tensile stress and strain above a neutral axis 260 and relatively high compressive stress and strain below neutral axis 260. Alternatively, when a stent is compressed, section 205 has relatively high tensile stress and strain below neutral axis 260 and relatively high compressive stress and strain above neutral axis 260.

The description and analysis relating to stress and strain distribution in a medical device is not limited to the structures in FIGS. 2A-C, 3, and 4. Analysis of strain distribution in a device, or generally any structure, subjected to applied stress may be performed for a device or structure of virtually any geometry As indicated above, high strain regions of polymeric stents, such as section 70 in FIGS. 2A-C, section 155 in FIG. 3, and section 205 in FIG. 4, may be susceptible to cracking during crimping or expansion of a stent. In general, the resistance to strain of the high strain region may be increased by increasing the flexibility of the region.

Certain embodiments of a structural element of a stent may include a flexible section embedded within a high strain region of the structural element. As noted above, a high strain region (e.g., section 70 in FIG. 2A) may have a higher strain as compared to other regions of the structural element when the stent is subjected to an applied stress during use.

In an embodiment, the flexible section may extend through the high strain region from an abluminal surface of the high strain region to a luminal surface of the high strain region. Generally, the abluminal and luminal surfaces of a stent tend to be in or substantially in a bending plane or surface of a structural element of a stent.

The flexible section may have a greater flexibility than a majority of the structural element outside of the flexible section. In particular, the flexible section may be less brittle (or not brittle at all) and may have a lower modulus than a majority of the structural element outside of the flexible section. The flexible section may also have a $T_g$ at or below body temperature. Thus, a more flexible material in the flexible section may tend to be more resistant to the high strain in the high strain region during use of a stent.

As indicated above, applied stresses during use such as crimping, delivery and deployment cause deformation or strain in the structural elements of a stent. High strain regions may correspond to regions of structural elements that are configured to bend when stress is applied to a stent during use. Such stresses may arise from crimping, delivery, deployment, and beating of the heart. Examples of such high strain regions are sections 20, 25, and 30 in FIG. 1A.

In some embodiments, the flexible section may be selectively positioned to inhibit or prevent fracturing in the high strain region when subjected to the applied stress during use. One embodiment may include the flexible section selectively positioned proximate a center of a width of an abluminal surface and a luminal surface in the high strain region of the structural element. As indicated above, (See FIG. 3) a neutral axis of a high strain region of a stent may be at or proximate a center of a width of an abluminal and luminal surface. Therefore, in some embodiments the flexible section may be selectively positioned proximate a neutral axis of the high strain region of the structural element. In order to adequately increase the resistance to strain of the high strain region, it is advantageous for the flexible section go all the way through the high strain region from the abluminal to the luminal surface. However, in some embodiments, the section may go partially through the thickness of the high strain region, either from the abluminal or the luminal surface.

A cross-section of the flexible section in a plane of the abluminal/luminal surface may be a variety of shapes, e.g., long and narrow; circular; oval; etc. In one embodiment, the flexible section may be slot-shaped or long and narrow, and positioned along at least a portion of a length of the high strain region. In some embodiments, the cross section of the flexible section can vary through the thickness of the stent.

Figure 6:
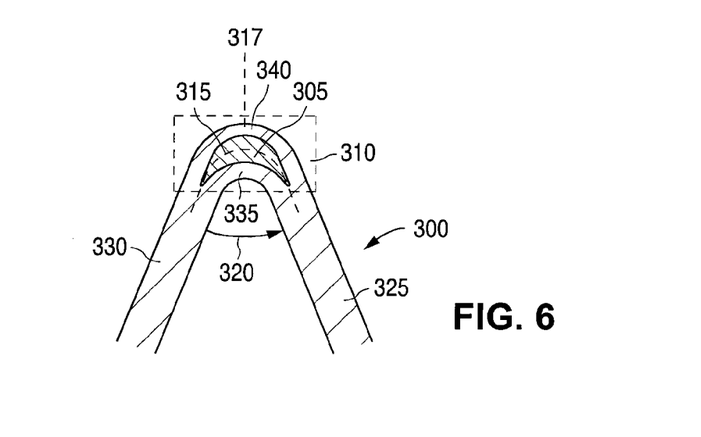
FIG. 6 depicts a side view of a portion of a stent with a flexible section.

FIG. 6 depicts a portion 300 of a structural element that has a flexible section 305 in a high strain region 310 of portion 300. Region 310 has a neutral axis 315. Angle 320 is the angle between an arm 325 and an arm 330 of portion 300.

The flexible section may separate at least a portion of the high strain region into three sections: flexible section 305, rigid section 335, and rigid section 340. The separation of a portion of the high strain region into three sections may facilitate, allow, and/or increase independent movement of arms 325 and 330. The flexible section may also tend allow arms 325 and 330 to bend with greater flexibility.

Figure 7:
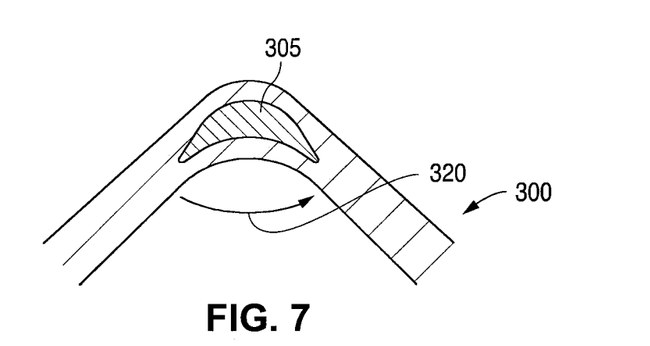
FIG. 7 depicts a side view of an expanded portion of a stent with a flexible section.
Figure 8:
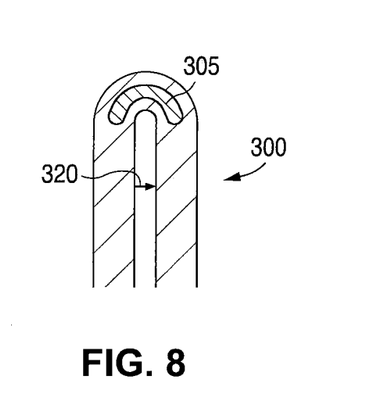
FIG. 8 depicts a side view of a compressed portion of a stent with a flexible section.

FIG. 7 depicts portion 300 of FIG. 6 when it is expanded. Similarly, FIG. 8 depicts portion 300 when it is compressed. As illustrated in FIGS. 7 and 8, it is expected that the area of flexible section 305 changes as portion 300 bends, i.e., changes as a function of angle 320 between arms 325 and 330. The change in the area is due to the difference in stress-strain behavior of flexible section 305 and sections of portion 300 surrounding flexible section 305, i.e., sections 335 and 340, and the rest of the portion 300. Flexible section 305 has a lower modulus and is less brittle than sections 335 and 340 and the rest of portion 300.

In some embodiments, the width of the flexible section may be relatively constant along the length of the high strain region. Alternatively, it may be desirable for the width of the flexible section to vary along the length of the high strain region. As depicted in FIG. 6, the width of flexible section 305 when portion 300 is unstressed is widest at a plane of bending symmetry 317 and decreases with distance from plane 317.

It may be advantageous for the width of the flexible section along the length of the high strain region to be directly proportional to a magnitude of the strain along the high strain region when the structural element is under stress. Therefore, a flexible section may be widest at or proximate to the center of a bending portion of the high strain region and decrease in either direction along a length of the high strain region.

In certain embodiments, a high strain region may have two or more flexible sections. In one embodiment, the two or more flexible sections may be positioned at or proximate a center of a width of an abluminal surface and luminal surface of the structural element. The two or more flexible sections may be proximate a neutral axis of the high strain region of the structural element. Multiple cavities may allow reduction in strain in the high strain region with less reduction in strength of the structural element. The flexible sections may be the of similar shape and depth or vary in shape and/or depth.

Figure 9:
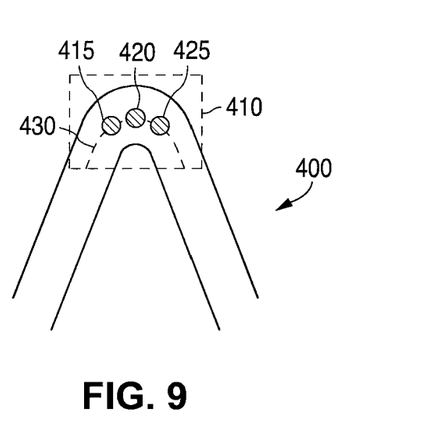
FIG. 9 depicts a side view of a portion of a stent with multiple flexible sections.

As an illustration, FIG. 9 depicts a portion 400 of a structural element that has flexible sections 415, 420, and 425 in a high strain region 410 of portion 400 that has a neutral axis 430.

Figure 10:
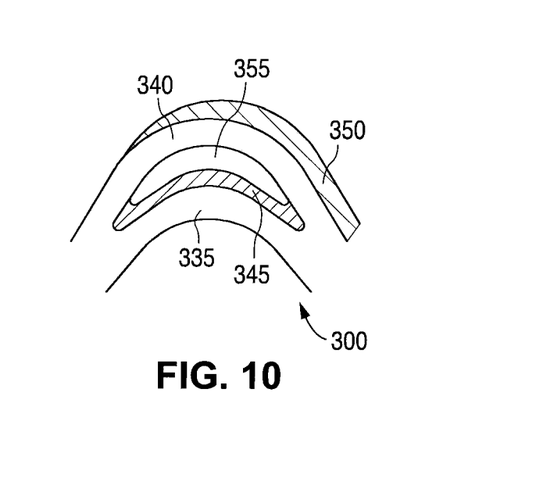
FIG. 10 depicts a three-dimensional side view of a portion of a stent with a cavity.

In certain embodiments, a method of forming a flexible section in a structural element of a stent may include forming a cavity within a high strain region of a structural element. The cavity may extend through the high strain region from an abluminal surface of the high strain region to a luminal surface of the high strain region. For example, the cavity may be formed by laser cutting the cavity in the high strain region. As an illustration, FIG. 10 depicts a portion 300 of a structural element with a cavity 355. FIG. 10 shows an interior surface 345 of section 335 and exterior surface 350 of section 340.

Additionally, the method may further include forming a flexible section within all or substantially all of the cavity. The flexible section may be formed by depositing a polymer or a polymer-solvent mixture into the cavity. A polymer-solvent mixture may be deposited, for example, by dipping, spraying, or controlled deposition.

A controlled deposition system can be used that applies various substances only to certain targeted portions of an implantable medical device such as a stent. A representative example of such a system, and a method of using the same, is described in U.S. Pat. No. 6,395,326 to Castro et al. A controlled deposition system can be capable of depositing a substance in or on an implantable medical device having a complex geometry, and otherwise apply the substance so that coating is limited to particular portions of the device. The system can have a dispenser and a holder that supports the medical substrate. The dispenser and/or holder can be capable of moving in very small intervals, for example, less than about 0.001 inch. Furthermore, the dispenser and/or holder can be capable of moving in the x-, y-, or z-direction, and be capable of rotating about a single point.

The controlled deposition system can include a dispenser assembly. The dispenser assembly can be a simple device including a reservoir which holds a composition prior to delivery, and a nozzle having an orifice through which the composition is delivered. One exemplary type of a dispenser assembly can be an assembly that includes an ink-jet-type printhead. Another exemplary type of a dispenser assembly can be a microinjector capable of injecting small volumes ranging from about 2 to about 70 nL, such as NanoLiter 2000 available from World Precision Instruments or Pneumatic PicoPumps PV830 with Micropipette available from Cell Technology System. Such microinjection syringes may be employed in conjunction with a microscope of suitable design.

A polymer-solvent mixture can also be selectively deposited by an electrostatic deposition process. Such a process can produce an electrically charged or ionized coating substance. The electric charge causes the coating substance to be differentially attracted to the device, thereby resulting in higher transfer efficiency. The electrically charged coating substance can be deposited into or onto selected regions of the device by causing different regions of the device to have different electrical potentials.

Furthermore, selective deposition of an implantable medical device may be performed using photomasking techniques. Deposition and removal of a mask can be used to selectively deposit substances into or onto surfaces of substrates. Masking deposition is known to one having ordinary skill in the art.

Furthermore, some embodiments may include enhancing adhesion between the flexible section and adjacent sections of the structural element to inhibit separation or delamination. One embodiment of improving adhesion may include allowing at least a portion of a flexible section to mix with at least a portion of adjacent sections. For example, a polymeric material for the flexible section may be selected to be miscible with the polymeric material of adjacent sections within a particular temperature range.

In an embodiment, the temperature during or after deposition of polymer-solvent mixture into a cavity in a high strain region may be selected so that mixing of polymers occurs at and near an interface of the flexible section and adjacent sections. As a result of the mixing of polymers in an interfacial region, there may be a gradual transition in composition, and hence, in mechanical and other properties normal to the interfacial region between layers. A gradual transition in properties in an interfacial region may inhibit or prevent separation or delamination of the flexible section from a structural element.

EXAMPLE

Some embodiments of the present invention are illustrated by the following examples. The examples are being given by way of illustration only and not by way of limitation. The parameters are not to be construed to unduly limit the scope of the embodiments of the invention.

A structural element may be composed of a high modulus polymer such as poly(L-lactide), poly(D,L-lactide), or poly(ε-caprolactone), mixtures thereof, or copolymers thereof. A flexible section may composed of flexible polymers such as poly(D,L-lactide)-polyethylene glycol-poly(D,L-lactide) triblock copolymer, 70/30 poly(L-lactide-co-trimethylene carbonate), or polyanhydrides.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of increasing the resistance to cracking in a high strain region of a balloon expandable polymer stent, the stent being formed from a first bioabsorbable polymer material, comprising the steps of:

forming a cavity in the high strain region of the stent, wherein the cavity is surrounded entirely by an interior sidewall surface formed by cutting some of the first bioabsorbable material from the high strain region; and disposing a second bioabsorbable polymer material within the cavity, the second bioabsorbable polymer material having a modulus that is less than the modulus of the first bioabsorbable polymer material;

wherein the cavity is located in a region where the centroidal axis of a strut does not coincide with the strut's neutral axis in bending when the stent is being radially compressed or expanded;

wherein the cavity is long and narrow and has a variable width over a length of the high strain region, wherein the width is proportional to a magnitude of strain along the high strain region and the width is a maximum at a plane of bending symmetry for the strut; and wherein the cavity has a size to inhibit or prevent fracture when the stent is crimped or expanded from a balloon.

2. The method of claim 1, wherein the second bioabsorbable polymer material has a glass transition temperature below the glass transition temperature of the first bioabsorbable polymer material.

3. A method for increasing the crack resistance of a structural element of a polymer stent, comprising the steps of:
- locating a region of high strain for the structural element when the stent is being crimped or expanded from a crimped state, wherein the high strain region is a curved section joined by two straight sections, and wherein the structural element is made of a first bioabsorbable polymer material;
- forming a cavity in the high strain region, the cavity extending from a luminal to an abluminal surface of the structural element; and
- disposing a second bioabsorbable polymer material within the cavity, the second bioabsorbable polymer material having a modulus that is less than the modulus of the first bioabsorbable polymer material;
- wherein the cavity is located in a region where the centroidal axis of the structural element does not coincide with the structural element's neutral axis in bending when the stent is being radially compressed or expanded; and
- wherein the cavity is long and narrow and has a variable width over a length of the high strain region, wherein the width is proportional to a magnitude of strain along the high strain region and the width is a maximum at a plane of bending symmetry for the strut.

4. The method of claim 3, wherein the disposing the second bioabsorbable polymer material within cavity step includes a material made from the same or different material as the first bioabsorbable polymer material heated to a temperature above a glass transition temperature for the second bioabsorbable polymer material whereupon a modulus of the second bioabsorbable polymer material is decreased.

5. A method of making a balloon-expandable stent, comprising:
- locating a region of high strain for a structural element when the stent is being crimped or expanded from a crimped state, wherein the structural element is made of a first bioabsorbable polymer material;
- forming a cavity in the structural element, the cavity being located in a region where the centroidal axis of the structural element does not coincide with the structural element's neutral axis in bending when the stent is being crimped or expanded from a crimped state; and
- disposing a second bioabsorbable polymer material within the cavity, the second bioabsorbable polymer material having a modulus that is less than the modulus of the first bioabsorbable polymer material;
- wherein the flexibility of the structural element is substantially more than a flexibility of the structural element not having the cavity; and
- wherein the cavity is long and narrow and has a variable width over a length of the high strain region, wherein the width is proportional to a magnitude of strain along the high strain region and the width is a maximum at a plane of bending symmetry for the strut.

6. The method of claim 3, wherein the second bioabsorbable polymer material has a glass transition temperature below the glass transition temperature of the first bioabsorbable polymer material.

7. The method of claim 5, wherein the second bioabsorbable polymer material has a glass transition temperature below the glass transition temperature of the first bioabsorbable polymer material.

* * * * *